(12) United States Patent
Wang et al.

(10) Patent No.: US 11,138,792 B2
(45) Date of Patent: Oct. 5, 2021

(54) MULTI-DIMENSIONAL METHOD OF FUNDAMENTAL SOLUTIONS FOR RECONSTRUCTION OF ELECTROPHYSIOLOGICAL ACTIVITY

(71) Applicant: CARDIOINSIGHT TECHNOLOGIES, INC., Independence, OH (US)

(72) Inventors: Yong Wang, St. Louis, MO (US); Qingguo Zeng, Solon, OH (US); Ping Jia, Solon, OH (US); Qing Lou, Powell, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 638 days.

(21) Appl. No.: 15/943,133

(22) Filed: Apr. 2, 2018

(65) Prior Publication Data
US 2019/0304186 A1   Oct. 3, 2019

(51) Int. Cl.
*G06T 17/30* (2006.01)
*G16H 30/40* (2018.01)
(Continued)

(52) U.S. Cl.
CPC .............. *G06T 17/30* (2013.01); *A61B 5/327* (2021.01); *A61B 5/339* (2021.01); *G16H 30/40* (2018.01);
(Continued)

(58) Field of Classification Search
CPC ............................ G06T 17/30; A61B 5/04028
(Continued)

(56) References Cited

U.S. PATENT DOCUMENTS

| 5,146,926 A | 9/1992 | Cohen |
| 5,483,968 A | 1/1996 | Adam et al. |

(Continued)

FOREIGN PATENT DOCUMENTS

| EP | 2745773 A3 | 7/2014 |
| WO | 2003/028801 A2 | 4/2003 |

(Continued)

OTHER PUBLICATIONS

Applicant: CardioInsight Technologies, Inc.; PCT International Application No. PCT/US2019/018311; Filing Date: Feb. 15, 2019; PCT International Search Report and PCT Written Opinion; Authorized Officer: Yeonkyung Kim; Date of Completion: Jun. 11, 2019; 12 pgs.

(Continued)

*Primary Examiner* — Nadia A Mahmood
(74) *Attorney, Agent, or Firm* — Tarolli, Sundheim, Covell & Tummino LLP

(57) ABSTRACT

In an example, an n-dimensional method of fundamental solution (MFS) is used to compute reconstructed electrical activity on a cardiac envelope based on geometry data and electrical data, where n is a positive integer greater than three. The electrical data represents electrical activity measured non-invasively from a plurality of locations distributed on a body surface of a patient, and the geometry data represents three-dimensional body surface geometry for the locations distributed on the body surface where the electrical activity is measured and three-dimensional heart geometry for the cardiac envelope.

26 Claims, 9 Drawing Sheets

(51) Int. Cl.
    *A61B 5/327*      (2021.01)
    *A61B 5/339*      (2021.01)
    *A61N 1/05*      (2006.01)
    *A61B 5/363*      (2021.01)

(52) U.S. Cl.
    CPC ............. *A61B 5/363* (2021.01); *A61N 1/0587* (2013.01); *G06T 2210/41* (2013.01)

(58) Field of Classification Search
    USPC ........................................................ 600/523
    See application file for complete search history.

(56) References Cited

U.S. PATENT DOCUMENTS

| | | |
|---|---|---|
| 6,047,206 A | 4/2000 | Albrecht et al. |
| 6,718,291 B1 | 4/2004 | Shapiro et al. |
| 6,772,004 B2 | 8/2004 | Rudy |
| 6,856,830 B2 | 2/2005 | He |
| 6,975,900 B2 | 12/2005 | Rudy et al. |
| 7,016,719 B2 | 3/2006 | Rudy et al. |
| 78,419,686 | 4/2013 | Sadowski et al. |
| 8,682,626 B2 | 3/2014 | Ionasec et al. |
| 9,427,587 B2 | 8/2016 | Ramanathan et al. |
| 2002/0128565 A1 | 9/2002 | Rudy |
| 2003/0120163 A1 | 6/2003 | Rudy et al. |
| 2004/0082870 A1* | 4/2004 | Rudy .................. A61B 5/6855 600/509 |
| 2008/0058657 A1 | 3/2008 | Schwartz et al. |
| 2008/0114257 A1 | 5/2008 | Molin et al. |
| 2009/0053102 A2 | 2/2009 | Rudy et al. |
| 2000/0227840 | 9/2000 | Uchiyama et al. |
| 2009/0275827 A1 | 11/2009 | Aiken et al. |
| 2010/0191131 A1 | 7/2010 | Revishvili et al. |
| 2012/0004540 A1 | 1/2012 | Liu et al. |
| 2013/0197884 A1 | 8/2013 | Mansi et al. |
| 2014/0235986 A1 | 8/2014 | Harlev et al. |
| 2015/0073268 A1 | 3/2015 | Stopek et al. |
| 2015/0133759 A1 | 5/2015 | Govari |
| 2016/0354012 A1 | 12/2016 | Zeng et al. |

FOREIGN PATENT DOCUMENTS

| | | |
|---|---|---|
| WO | 2005/072607 A1 | 8/2005 |
| WO | 2008/085179 A1 | 7/2008 |
| WO | 2012/109618 A2 | 8/2012 |
| WO | 2014/118535 A3 | 8/2014 |

OTHER PUBLICATIONS

H.S. Oster, B. Taccardi, R.L. Lux, P.R. Ershier, Y. Rudy, "Noninvasive Electrocardiographic Imaging: Reconstruction of Epicardial Potentials, Electrograms and Isochrones, and Localization of Single and Multiple Electrocardiac Events", Circulation 1997; 96:1012-1024.

J.E. Bumes, B. Taccardi, Y. Rudy, "A Noninvasive Imaging Modality for Cardiac Arrhythmias" Circulation Oct. 24, 2000; 102: 2152-2158.

C. Ramanathan, R.N. Ghanem, P. Jia, K. Ryu, Y. Rudy, "Electrocardiographic Imaging (ECGI): A Noninvasive Imaging Modality for Cardiac Electrophysiology and Arrhythmia" Nature Medicine, Mar. 2004; 10:422-428.

A. Eisenberg, Beyond the EKG, to a Hypersensitive heart monitor. New York Times. Apr. 22, 2004.

M.A. Goldberg and C.S. Chen, The Method of Fundamental Solutions for potential, Helmholtz and diffusion problems, in Boundary Integral Methods—Numerical and Mathematical Aspects, ed. M.A. Goldberg, Computational Mechanics Publications, 1998, DD. 103-176.

M.A. Goldberg, C.S. Chen & A.S. Muleshkov, The Method of Fundamental solutions for diffusion equations, Boundary Element Technology XIII, eds. C.S. Chen, C.A. Brebbia, D.W. Pepper, WIT Press, Boston, Southampton, pp. 377-386, 1999.

Y.C. Hon, T. Wei, A fundamental solution method for inverse heat conduction problems. Engineering Analysis with Boundary Elements, vol. 28, Issue 5, pp. 489-495, May 2004.

Y.C. Hon and T. Wei, "The method of fundamental solution for solving multidimensional inverse heat conduction problems," CMES-Comp. Model. Eng. 7, 119-132 (2005).

Divo et al.; "A Mesh less Method for Conjugate Heat Transfer Problems"; Engineering Analysis with Boundary Elements 29 (2005) 136-149.

Fischer, G. et al., "Application of high-order boundary elements to the electrocardiographic inverse problem", Computer Methods and Programs in Biomedicine Elsevier Ireland, vol. 58, No. 2, (1999) pp. 119-131.

Karageorghis, Andreas and Fairweather, Graeme, "The Method of Fundamental Solutions for the Numerical Solution of the Biharmonic Equation", Journal of Computation Physics, London, GB, vol. 69, No. 2, Apr. 1, 1987 (Apr. 1, 1987), pp. 434-459.

Seger, M. et al., Lead Field Computation for the Eletrocardiographic inverse problem—finite elements versus boundary elements : Computer Methods and Programs in Biomedicine Elsevier Amsterdam, NL, vol. 77, No. 3, Mar. 1, 2005 (Mar. 1, 2005), pp. 241-252.

Rudy Y., et al.: "The Inverse Problem in Electrocardiography: Solutions in Terms of Epicardial Potentials", Critical Reviews in Biomedical Engineer, CRC Press, Boa Raton, FL, US, vol. 16, No. 3, Jan. 1, 1988, pp. 215-268.

Jeongjin Roh, High-Performance Error Amplifier for Fast Transient DC-DC Converters, Express Briefs, vol. 52, No. 9, Sep. 2005.

Ye [Scedil] Im Serinagaoglu et al.: "Multielectrode Venous Catheter Mapping as a High Quality Constraint for Electrcardiographic Inverse Solution", Journal of Electrocardiology, vol. 35, No. 4, Oct. 1, 2002, pp. 55-73.

Geneser, et al: "The Influence of Stochastic Organ Conductivity in 20 ECG Forward Modeling: A Stockhastic Finite element Study", Engineering in Medicine and Biology Society, 2005. IEEE-EMBS 2005. 27th Annual International Conference of the Shanghai, China Sep. 1-4, 2005, Piscataway, NJ,VUSA, IEEE, Jan. 1, 2005, pp. 5528-5531.

Yong Wang, "Contributions to the Methodology of Electrocardiographic Imaging (ECGI) and Application of ECGI to Study Mechanisms of Atrial Arrhythmia, Post Myocardial Infarction Electrophysiological Substrate, and Ventricular Tachycardia in Patients"; All Theses and Dissertations (ETDs), 361; http://openscholarship.wustl.edu/etd/361; (Jan. 2009); 228 pgs.

\* cited by examiner

MULTI-DIMENSIONAL METHOD OF FUNDAMENTAL SOLUTIONS FOR RECONSTRUCTION OF ELECTROPHYSIOLOGICAL ACTIVITY

TECHNICAL FIELD

This disclosure relates to multi-dimensional meshless reconstruction electrophysiological activity on a surface of interest.

BACKGROUND

The inverse problem can be solved to reconstruct electrical activity inside a body surface based measured electrical activity on the body surface. One example of such an application relates to electrocardiographic imaging where electrical potentials measured on a torso can be combined with geometry information to reconstruct electrical potentials on a cardiac surface. For example, a computer can be programmed to combine and process the body surface electrical potential data and the geometry data to reconstruct estimates of the cardiac surface electrical potentials (e.g., epicardial potentials). The reconstructed cardiac surface potentials may in turn be processed to generate one or more epicardial cardiac surface potential maps, epicardial cardiac surface electrograms, and epicardial cardiac surface isochrones.

SUMMARY

In an example, a system includes memory and one or more processors. The memory is to store data and executable instructions. The data includes electrical data representing electrical activity measured from a plurality of locations distributed on the body surface. The data further includes geometry data representing body surface geometry of the locations distributed on the body surface where the electrical activity is measured and geometry of a cardiac envelope. The processor is to access the memory and execute the instructions to at least reconstruct electrical activity on to the cardiac envelope based on the geometry data and the electrical data. The reconstructed electrical activity is computed using an n-dimensional method of fundamental solution, where n is a positive integer greater than three.

In another example, an n-dimensional method of fundamental solution (MFS) is used to compute reconstructed electrical activity on a cardiac envelope based on geometry data and electrical data, where n is a positive integer greater than three. The electrical data represents electrical activity measured non-invasively from a plurality of locations distributed on a body surface of a patient, and the geometry data represents three-dimensional body surface geometry for the locations distributed on the body surface where the electrical activity is measured and three-dimensional heart geometry for the cardiac envelope.

DETAILED DESCRIPTION

Figure 1:
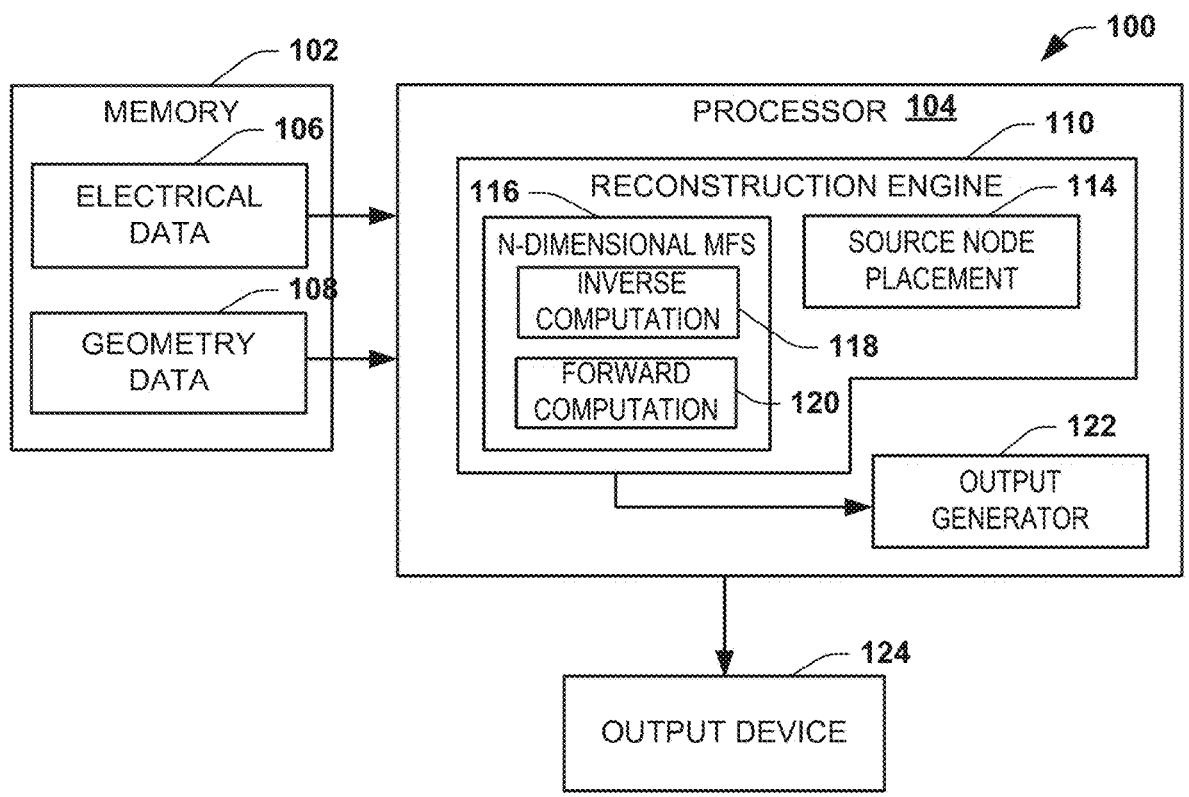
FIG. 1 illustrates an example of a system to reconstruct electrical activity on a surface.

This disclosure relates to reconstructing electrical activity on a surface of interest using an n-dimensional Method of Fundamental Solution (MFS). The value of n may be any positive integer greater than three, although for purposes of consistency is described as set to four (n=4), such that the MFS is computed in a spatial domain located outside of a three-dimensional space where physical boundaries exist. As an example, the physical boundaries may include three-dimensional spatial geometry of a cardiac envelope and locations on a body surface where electrical activity is measured non-invasively. The systems and methods disclosed herein are thus configured to utilize the n-dimensional method of fundamental solution to compute reconstructed electrical activity on the cardiac envelope.

By way of example, the geometry of a cardiac envelope and locations on a body surface where electrical activity is measured (e.g., by an arrangement of electrodes) may be represented in a three-dimensional spatial domain. Corresponding cardiac nodes can be determined on the cardiac envelope to define the locations on the cardiac envelope for which the reconstructed cardiac electrical activity apply. The geometry data, including the body surface geometry and the geometry of the cardiac envelope in a domain, to corresponding geometry in a three-dimensional subspace of the n-dimensional (e.g., 4D) domain. That is the three-dimensional geometry is defined as a three-dimensional subspace (e.g., a hyperplane) along in the n-dimensional space. As a further example, a plurality of source nodes (e.g., also referred to as virtual sources or fictitious points) are determined in the nth-dimension outside of the three-dimensional subspace of the corresponding three-dimensional geometry. Some of such source nodes define body surface source nodes (e.g., residing on a virtual boundary) in a first three-dimensional subspace of the n-dimensional domain and another plurality of the source nodes define cardiac source nodes (e.g., residing on another virtual boundary) in a second three-dimensional subspace of the n-dimensional domain. An analytical expression for the MFS is derived to produce a matrix A. The matrix A relates a location of each source node to the locations distributed on the body surface (e.g., body surface nodes at the center of electrodes) where the electrical activity is measured and relates a location of each cardiac source node to the locations on the cardiac envelope for which the reconstructed cardiac electrical activity applies. An inverse computation is performed (e.g., via a regularization or other appropriate mathematical technique) on the A matrix and the electrical data (e.g., the noninvasively measured electrical activity) to compute a plurality of source node coefficients.

A forward computation is used to determine the electrical activity on the cardiac envelope. For example, a matrix of coefficients B is computed to translate the source node coefficients to the electrical activity at the cardiac nodes on the cardiac envelope. The matrix B relates each cardiac node location to each source node location. Once matrix B and the source node coefficients (determined by the inverse computation) are determined, a straightforward calculation can be performed to compute the cardiac electrical activity on the cardiac envelope. Because the source nodes reside in 4D space outside of the subspace of the cardiac and body surface nodes, greater flexibly is afforded in placing the source nodes. This further enables the nodes on the cardiac envelope to be selected to include any structure on or inside the heart.

By way of example, the cardiac envelope may be selected as an epicardial surface, an endocardial surface or a combination of endocardial and epicardial surfaces. Additionally or alternatively, the cardiac envelope onto which the electrical activity is reconstructed may include structures other than epicardial and/or endocardial. For example, the envelope can correspond to anatomical geometry of various cardiac structures within the ventricles and atrium, such as papillary muscles, septum, Bundle of His, bundle branches, Purkinje fibers, trabeculae carneae, moderator band and/or other structures that reside within the heart. In some examples, the structures may be selected (e.g., in response to a user input) to include tissue structure residing along an electrical conduction pathway for the heart.

From a mathematical perspective, the systems and methods in this disclosure provide solutions to the Cauchy problem for the Laplace equation. For example, rather than employing a surface mesh of the body surface and heart surface as in the boundary element method or being constrained within a three-dimensional spatial domain, the approach disclosed extends MFS to defines virtual source nodes in an n-dimensional space beyond three-dimensional space. Based on the known geometrical relationships between the virtual source nodes, the positions where the body surface potentials are measured (e.g., via electrodes), and the nodes on one or more cardiac surfaces for which the heart surface electrical potentials are computed, the n-dimensional MFS technique can readily reconstruct the epicardial cardiac surface potentials from the measured body surface potentials. Moreover, by placing virtual source nodes in the 4D space, the approach further can overcome the limitation of existing MFS methods in reconstructing electrical activities on the cardiac envelope, which may include one or more endocardial surfaces as well as other structures within the heart (e.g., structures within the ventricles and atrium, such as papillary muscles, septum, Bundle of His, bundle branches, Purkinje fibers, trabeculae carneae, moderator band or other structures that reside within the heart that provide electrical conduction).

FIG. 1 depicts an example of a system 100 that is configured to reconstruct electrical activity on one or more surface of interest based on electrical activity measured on another (different surface). In some examples, the surface of interest is a cardiac envelope. As used herein, a cardiac envelope may refer to any two-dimensional or three-dimensional surface or surfaces residing inside the patient's body on to which electrical signals are to be reconstructed. As one example, the surface corresponds to a virtual surface (e.g., a sphere or other three-dimensional structure). As another example, the surface corresponds to one or more surfaces of an anatomical structure, such as an epicardial surface, an endocardial surface or both epicardial and endocardial surfaces. The cardiac envelope thus may be configured as a cardiac surface model having three-dimensional geometry that is registered in or can be registered into a frame of reference of a patient's anatomy. The cardiac surface model may include a cardiac nodes distributed across the geometry representing the cardiac envelope.

In the example of FIG. 1, the system 100 is demonstrated as a computing apparatus that includes memory 102 and a processor 104. The memory 102 is configured to store data and instructions. The processor 104 is configured to access the memory and execute the instructions to perform the methods and functions disclosed herein. The memory 102 stores electrical data 106 such as representing electrical signals measured from the body surface over one or more time intervals. The electrical data 106 may include real time measurements of the electrical activity provided from an arrangement of electrodes and/or previous measurements, which generally may vary depending on whether the system 100 is being utilized for real time analysis (e.g., during an electrophysiological study) or post-procedure analysis.

The memory also stores geometry data 108. The geometry data 108 includes data representing body surface geometry for the locations distributed on the body surface where the electrical activity is measured. For example, the locations on the body surface correspond to respective electrode locations of a sensor array that is positioned on the patient's thorax and configured to sense body surface electrical activity from such electrode locations. Examples of a non-invasive sensor array that can be employed to measure body surface electrical activity are shown and described in U.S. Pat. No. 9,655,561, which was filed Dec. 22, 2011, and International patent application No. PCT/US2009/063803, which was filed Nov. 10, 2009, each of which applications is incorporated herein by reference.

The geometry data 108 includes data representing geometry of a cardiac envelope to which the reconstructed electrical activity applies. The cardiac envelope can correspond to a three dimensional epicardial surface geometry of a heart. Alternatively or additionally, the cardiac envelope can correspond to a three dimensional endocardial surface geometry of the heart. As yet another alternative, the cardiac envelope may correspond to virtually any geometric surface that resides between a region inside the patient's heart and the out surface of the patient's torso where the electrical measurements are taken. The geometry data 108 may correspond to actual patient anatomical geometry, a preprogrammed generic model or a combination thereof (e.g., a model that is modified based on patient anatomy).

As an example, the geometry data 108 may be derived from processing image data acquired for the patient via an imaging modality (not shown). For example, the imaging system 130 can be implemented according to any imaging modality, such as computed tomography (CT), magnetic resonance imaging (MRI), x-ray, fluoroscopy, ultrasound or the like, to acquire three-dimensional image data for the patient's torso. Such image processing can include extraction and segmentation of anatomical features, including one or more organs and other structures, from a digital image set. Additionally, a location for each of the electrodes in the sensor array 164 can be included in the geometry data 172, such as by acquiring the image while the electrodes are disposed on the patient and identifying the electrode locations in a coordinate system through appropriate extraction and segmentation. The imaging may be performed concurrently with recording the electrical activity that is utilized to generate the patient measurement data 170 or the imaging can be performed separately (e.g., before or after the measurement data has been acquired). In another example, one or more non-imaging based techniques can also be utilized to obtain a three-dimensional position of the electrodes in the coordinate system, such as a digitizer or manual measurements.

The processor 104 is configured to execute machine-readable instructions, demonstrated in the example of FIG. 1 as including a reconstruction engine 110 and an output generator 112. The reconstruction engine 110 is programmed to reconstruct electrical activity on to the cardiac envelope based on the geometry data 108 and the electrical data 106. As disclosed herein, the reconstructed electrical activity is computed using an n-dimensional MFS, where n is a positive integer greater than three (e.g., 4D MFS). The n-dimensional space, mathematically, defines one or more spatial dimensions beyond three-dimensional space. It is to be understood that, as used herein in connection with the MFS, "n" does not represent the time domain but another mathematical spatial domain. Nonetheless, the electrical data can be measured over time and the electrical activity that is ultimately reconstructed on to the surface of interest may extend over one or more time intervals. For example, the reconstruction engine 108 is configured to reconstruct electrical activity for a plurality of cardiac nodes spatially distributed over a cardiac envelope based on electrical data 110 measured non-invasively over one or more time intervals. In some examples, the number of cardiac nodes can be greater than 1,000 or 2,000 or more depending upon a desired resolution. For example, the surface region or regions that define the cardiac envelope and/or resolution of nodes on each such surface(s) may be set and stored in the geometry data 108 (or other data) in response a user input.

In the example of FIG. 1, the reconstruction engine 110 is programmed to include source node placement function 114 and an n-dimensional method of fundamental solution 116, which includes an inverse computation 118 and a forward computation 120. The n-dimensional MFS 116 utilizes the electrical data 106 and the geometry data 108. As mentioned, the geometry data is used to determine a plurality of cardiac nodes that define the locations on the cardiac envelope for which the reconstructed cardiac electrical is to apply. The geometry data 108 also includes body surface nodes that define the electrode locations where electrical activity is measured from the body surface to provide the electrical data 106.

By way of further example, the reconstruction engine 110 translates the geometry data 108, representing the body surface geometry and the geometry of the cardiac envelope in a three-dimensional spatial domain, to corresponding location in the n-dimensional domain. For example, the three-dimensional subspace for the spatial geometry is placed at a predetermined value of the nth dimension (e.g., at an origin or other location in the n-dimensional space). In this way, the cardiac nodes and the body surface nodes each is assigned a location corresponding to n coordinates in the n-dimensional space.

The source node placement function 114 is programmed to determine a plurality of source nodes (e.g., virtual nodes or fictitious points) in the nth-dimension outside of the three-dimensional subspace of the geometry data 108. For example, a portion of the source nodes defines body surface source nodes in a first three-dimensional subspace of the n-dimensional domain. Another portion of the source nodes defines cardiac source nodes in a second three-dimensional subspace of the n-dimensional domain. Thus, each of the subspace of the spatial geometry, the subspace of cardiac source nodes and the subspace of body surface source nodes are spaced apart from each other along the fourth dimension. By placing the source nodes in the nth dimension, in contrast to placement in the same three-dimensional space as the cardiac and body surfaces represented by the geometry data—like traditional MFS, the irregular and narrow geometry within the heart surface that constrain traditional MFS can be avoided. Thus, the systems and methods disclosed herein affords greater flexibility (e.g., nearly anywhere in the nth dimension) to optimize placement of source nodes than existing approaches, and thereby to improve the accuracy of the reconstruction on the cardiac envelope. For instance, the reconstruction engine 110 can control the distance between any and all of the subspace for spatial geometry, cardiac source nodes and body surface source nodes.

The n-dimensional MFS 116 is further programmed (e.g., to include or otherwise utilize a matrix calculator) to derive an analytical expression for the method of fundamental solution that includes a transfer matrix A. As disclosed herein, the matrix A includes coefficients that relate a location of each source node (e.g., including both cardiac source nodes and body surface source nodes) to the body surface node locations distributed on the body surface where the electrical activity is measured. The inverse computation 118 is programmed to perform an inverse computation on the A matrix and the noninvasively measured electrical activity provided by the electrical data 106 to compute a plurality of source node coefficients.

As a further example, the n-dimensional MFS 116 is programmed (e.g., to include or otherwise utilize another matrix calculator) to determine a matrix of coefficients B that relates each cardiac node location on the cardiac envelope to each source node location. The forward computation 120 is programmed to perform a forward computation based on the matrix B and the plurality of source node coefficients to compute the cardiac electrical activity on the cardiac envelope. The reconstruction engine may thus compute the electrical activity on the cardiac envelope for each of a plurality of consecutive time samples in one or more time intervals, such as to show how the electrical activity on the cardiac envelope changes over time.

The output generator 122 configured to generate corresponding output data that can in turn be rendered as a corresponding graphical output. For example, the output generator 122 provides the output data to a graphics pipeline of a computing device that supplies the graphical output via an interface to an output device 124. The output device may include a display (e.g., a screen, wearable augmented reality glasses, a heads up display or the like) configured to display a graphical visualization generated based on the reconstructed electrical activity that is produced. The graphical output further may include electrical activity (e.g., voltage potentials) reconstructed on the cardiac envelope or electrical characteristics derived from such reconstructed electrical activity. Because the n-dimensional MFS 116 is not constrained by placing the cardiac source nodes inside of the cardiac envelope as in existing 3D MFS approaches, in some examples, the cardiac envelope may include an endocardial surface, epicardial surface or a combination of both endocardial and epicardial surfaces. The electrical activity or derivations thereof thus can be displayed on the selected cardiac surface(s) and at a desired resolution.

Figure 2:
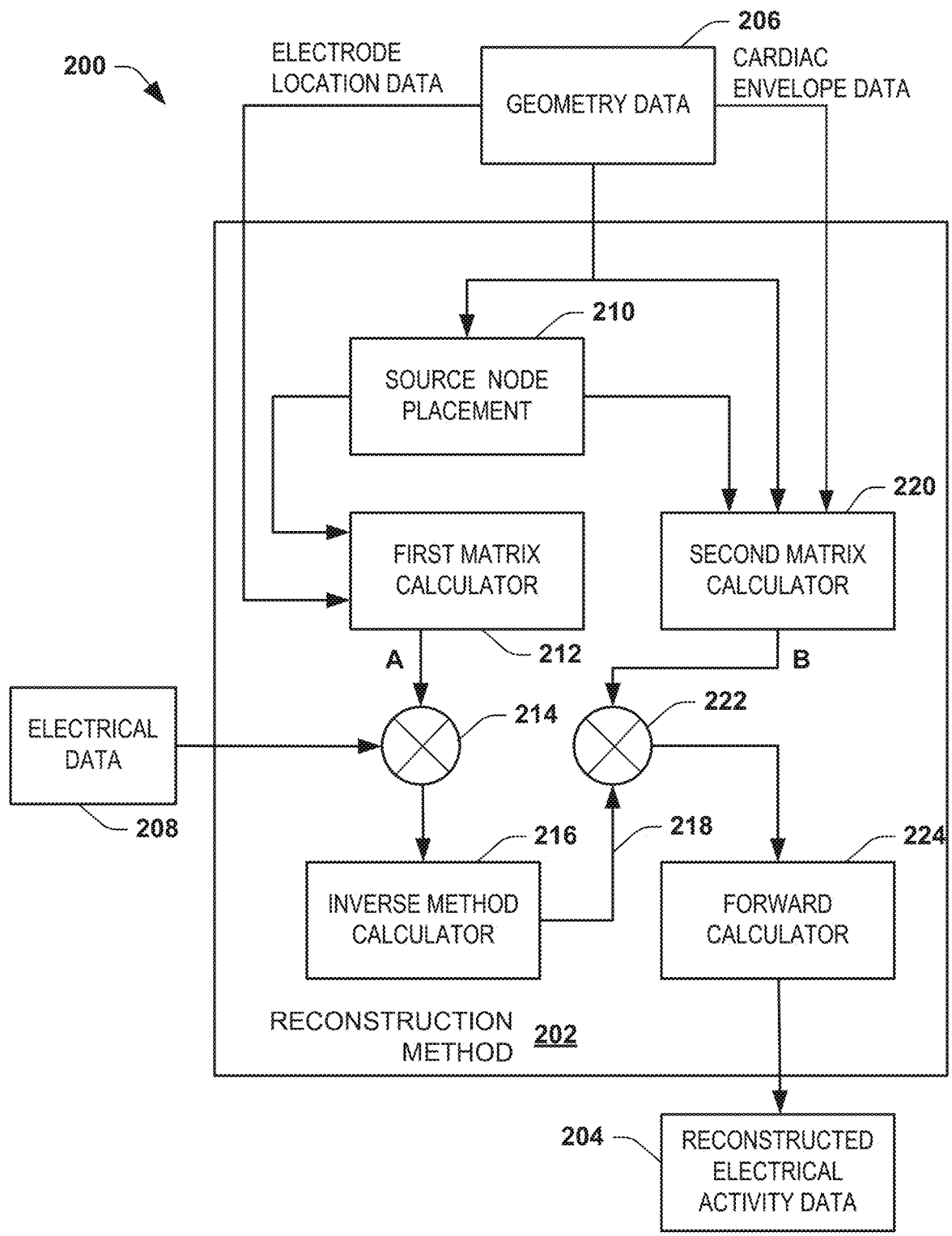
FIG. 2 depicts an example of a functional block diagram of a reconstruction method.

FIG. 2 depicts an example of a system 200 that is configured to reconstruct electrical activity on a cardiac envelope. The system 200 implements a reconstruction method 202, such as corresponding to the reconstruction engine 110 of FIG. 1, which is demonstrated as a workflow diagram of code elements that may be executed by one or more processors. In the example of FIG. 2, the reconstruction method 202 employs a four-dimensional (4D) MFS to compute reconstructed electrical activity data 204 based on geometry data 206 and electrical data 208. The geometry data 206 can be obtained from geometry determining device, such as disclosed herein (see, e.g., FIG. 3), to specify the geometrical relationship between the body surface, body surface electrode locations, and the cardiac envelope on which the electrical activity is being reconstructed. Additionally, the electrical data 208 can represent surface potential data measured by each electrode in an arrangement of electrodes (at body surface node locations represented the in geometry data). In this example, the three-dimensional locations and geometrical relationships of the structures represented in the geometry are translated into the $4^{th}$ dimension. That is, the cardiac envelope and its corresponding cardiac nodes as well as the body surface nodes (electrode locations) define locations in a three-dimensional subspace residing in the 4th dimension. 30

As a further example, the reconstruction method 202 includes a source node placement function 210 to determine locations of source nodes in the $4^{th}$ dimension, which are virtual or fictitious points used by the 4D MFS implemented by the reconstruction method 202. As disclosed herein, the source nodes can include cardiac source nodes and body surface source nodes. In some examples, the source node placement function 210 places the cardiac source nodes in the 4th dimension in a three-dimensional spatial arrangement and distribution that corresponds to the spatial arrangement and distribution of the cardiac nodes on the cardiac envelope in the three-dimensional subspace. Additionally or alternatively, the source node placement function 210 places the torso source nodes in the fourth dimension in the spatial arrangement and distribution that corresponds to a spatial distribution of electrode locations on the body surface where the electrical activity is measured. In other examples, the cardiac source nodes and the body surface source nodes may be determined in the fourth dimension with a different arrangement and distribution from their respective nodes. For instance, the source nodes may be greater or lesser in number than the respective cardiac and body surface nodes. The number of nodes and their spatial distribution can be set (e.g., to a default or user-programmable value) to provide a desired resolution for the resulting reconstructed electrical activity on the cardiac envelope. In some examples, the locations of the source nodes in the $4^{th}$ dimension can be optimized to be evenly distributed in the subspace.

As another example, the source node placement function 210 is configured to determine the location of the source nodes in the $4^{th}$ dimension by controlling the distance from each source node to corresponding geometry in the three-dimensional subspace. That is, the source node placement function 210 can place each of the nodes based a distance parameter that is set (e.g., to a fixed distance value or to within a range of values) based on a distance between source nodes and cardiac nodes and body surface nodes. For example, the source node placement function 210 determines the location of each body surface source node in the $4^{th}$ dimension such that it is located a predetermined distance from a corresponding body surface node. Additionally, the source node placement function 210 is configured to determine the location of each cardiac source node in the $4^{th}$ dimension such that it is located a predetermined distance from a corresponding cardiac node location on the cardiac envelope. As a further example, the source node placement function 210 further may be configured to control the distance between the cardiac source nodes and the body surface nodes as to approximate the distance between the torso source nodes in the $4^{th}$ dimension and the body surface nodes where the electrical activity is measured in three-dimensional subspace. In other examples, other distances may be used to control the placement of the source nodes and the geometry nodes in the 4-dimensional space.

The reconstruction method 202 also includes a first matrix calculator 212 programmed to compute a transfer matrix A that relates the location of each source node (e.g., determined by source node placement function 210) to the geometry to the body surface nodes, which correspond to locations distributed on the body surface where the electrical activity is measured. The coefficients in the transfer matrix A are reflect the "strength" of each source node. For example, that the measured electrical potential on the body surface may be expressed as a vector ($V_{BS}$):

$$V_{BS} = A\Gamma$$

where A is a 2N×P+1 matrix,
where N represents the total number of body surface nodes and
P represents the total number of source nodes.

In this example, the first matrix calculator 212 may be configured to compute the value of each entry ($a_{j,k}$) in the matrix A as a function of a square of the distance between each body surface node and each source node. For example, in 4-dimensional space, the value of each entry $a_{j,k}$ in matrix A is a function of the distance between body surface (e.g., torso) node ($TN_j$) and source node ($SN_k$) in 4D space, such that:

$$a_{j,k} = \frac{1}{r_{j,k}^2}$$

where $r_{j,k}$ equals the distance between a body surface node $TN_j$ and source node $SN_k$ in the 4-dimensional space. For example, the distance between each body surface node and each of the source nodes (e.g, each of the body surface source nodes and cardiac source nodes) may be computed between the respective 4D locations of such nodes according to a 4D Euclidean or other distance calculation. Because each value for $r_{j,k}$ is readily calculable in view of the known coordinates of each torso node and each source node, the entries $a_{j,k}$ in matrix A are likewise known.

A combinatorial function 214 of the reconstruction method 202 thus can employ the computed transfer matrix A to express the non-invasively measured electrical data 208 as a function of the transfer matrix A and $\Gamma$, as noted above. Therefore, the 1×P+1 vector $\Gamma$ is the only unknown in this expression. Accordingly, an inverse method calculator 216 is programmed to perform an inverse computation on the A matrix and the noninvasively measured electrical activity to compute a plurality of source node coefficients. In this way the inverse method calculator 216 determines the value of the inverse of the transfer matrix (e.g., $\Gamma = A^{-1} * V_{BS}$). Since the computation of $\Gamma$ is an ill-posed problem, the inverse method calculator 216 can employ any of variety of mathematical schemes to estimate the values in the matrix $\Gamma$. Examples of schemes that are believed to provide effective results for computing $\Gamma$ include Tikhonov zero order regularization and the Generalized Minimal Residual (GMRes) method. For example, the inverse method calculator 216 can be programmed to implement Tikhonov regularization, such as described in U.S. Pat. No. 6,772,004, or GMRes regularization, such as described in U.S. Pat. No. 7,983,743, each of which is disclosed herein by reference in its entirety.

The reconstruction method 202 also includes a second matrix calculator 220 to compute a matrix B. The matrix B operates to translate the source node coefficients determined via the inverse method calculator 216 to corresponding electrical activity on the cardiac envelope of interest at each cardiac node location (e.g., endocardial nodes and/or epicardial nodes). As an example, the value of each entry $b_{j,k}$ in matrix B is a function of the distance between each cardiac node $CN_j$ and source node $SN_k$, such that:

$$b_{j,k} = \frac{1}{r_{j,k}^2}$$

where $r_{j,k}$ equals the distance between cardiac node $CN_j$ and source node $SN_k$.

In the example of FIG. 2, another combinatorial function 222 thus can express the cardiac electrical activity as a function of the transfer matrix B and Γ, as noted determined above by the inverse method calculator 216. For example, the combinatorial function 222 can express the cardiac electrical activity on the cardiac envelope ($V_{CE}$) as a function of the matrix B and Γ, such as:

$$V_{CE} = B\Gamma$$

where B is a M×P+1 matrix,
where M represents the total number of cardiac nodes and P represents the total number of source nodes.

As the distance for each value for $r_{j,k}$ is readily calculable in 4D space, the entries in matrix B are all known, which allows for a straightforward calculation of $V_E$ from B and Γ. For example, a forward calculator 106 can be employed to compute the corresponding estimate of reconstructed electrical activity data 208 on the cardiac nodes distributed across the cardiac envelope. In some examples, the locations of the plurality of cardiac nodes are set, in response to a user input, such as to reside on a selected one or both of an epicardial surface and an endocardial surface or another cardiac envelope.

Figure 3:
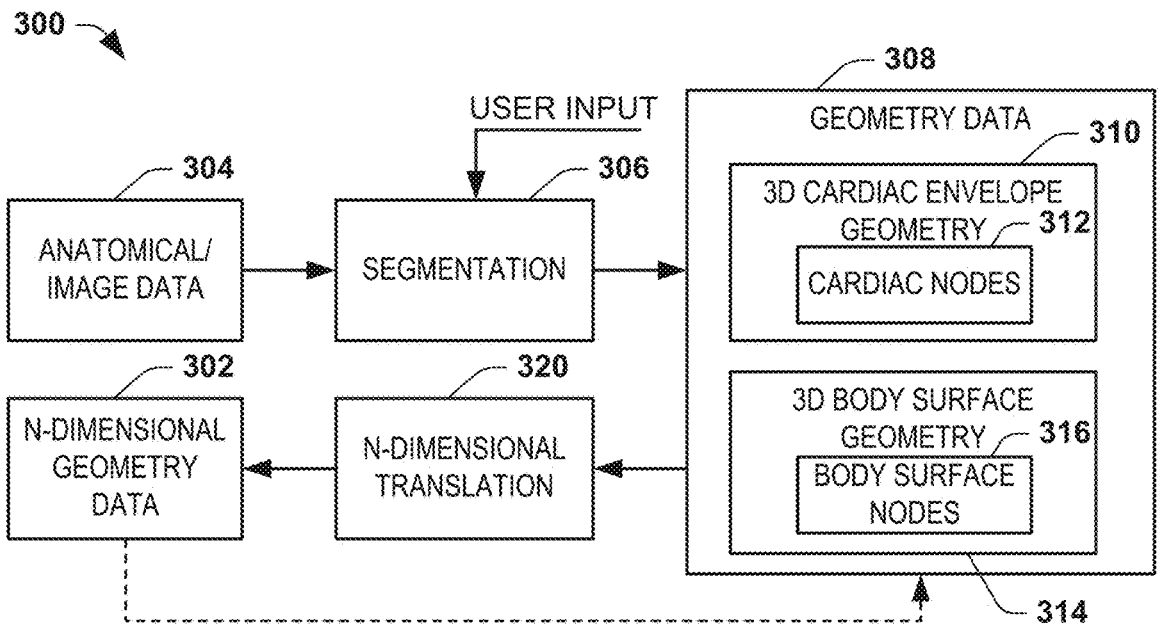
FIG. 3 depicts an example of converting geometry data.

By way of further example, FIG. 3 depicts an example of a geometry processing system 300 that can be utilized to provide N-dimensional geometry data 302 for the heart and body surface, such as corresponding to the geometry data described with respect to FIGS. 1 and 2. In the example of FIG. 3, anatomical and/or image data is provided as an input. The anatomical or image data, for example, may include 2D and/or 3D image data of patient anatomy, such as provided from an imaging modality as mentioned above. Additionally, in some examples, the body surface anatomical data in the data 304 may be provided by other measurement methods, such as a digitizer and/or manual measurements.

For the example of image data 304, such as 3D image data obtained via CT, MRI or other modality, a segmentation method 306 segments the anatomical/image data 304 to provide corresponding 3D geometry data 308. For example, the segmentation method 306 is programmed to identify surface boundaries for the body surface geometry and cardiac envelope geometry and provide corresponding 3D cardiac geometry 310 and 3D body surface geometry 314. The segmentation method 306 may be entirely automatic, or semiautomatic in which a user can identify and label points along the body surface, heart and heart surface, for example. The segmentation method 306 may be integrated as part of the imaging modality that supplies the data 304 or, in other examples, be connected to access the data 304 and implement the processing and segmentation of body surface and heart structures. Various open source software and commercially available software products (e.g., Amira 3D visualization software from Thermo Fischer Scientific, Inc. or others) can be used to identify, segment, and label the heart and heart surface to generate the 3D geometry data.

The segmentation method 306 applied to the anatomical/image data 304 may also be utilized to place cardiac nodes 312 on the cardiac envelope. The segmentation method 306 determines the cardiac nodes 312 to define the locations on the cardiac envelope for which the reconstructed cardiac electrical activity is to apply. The segmentation method 306 also determines the body surface nodes 314 at corresponding to locations (e.g., at centroids of electrodes) on the body surface where electrical activity is non-invasively measured.

As a further example, to place each cardiac node (CN), either a manual or automatic technique can be used to place a plurality M of CNs on the cardiac envelope. With a manual technique, for example, a user manually places the CNs at user-selected points along the cardiac envelope 502. With an automated technique, machine executable instructions are performed by a processor (e.g., processor 104) to automatically distribute the CNs along the cardiac envelope. The value of M will define the resolution of the n-dimensional MFS. For example, the value of M can be a default value or be set in response to a user input such that the MFS technique described herein exhibits a desired degree of resolution. As one example, M is set to 100, 500, 1000, 2000 or any number according to application requirements and desired resolution. In some examples, the CNs are evenly distributed spatially over the cardiac envelope 310. In other examples, it may be desirable to obtain high spatial resolution reconstruction in a certain region of the heart, in which case user may specify, in response to a user input, to concentrate more CNs in each such area relative to some other areas. For example, for analyzing atrial arrhythmia, a greater concentration of CNs may be placed in the atrial region of the heart, epicardially and/or endocardially.

As a further example, a user input may be supplied (e.g., via an input device, such as mouse, keyboard or voice control, to instruct the segmentation method 306 specify a cardiac envelope on which the cardiac nodes are to be placed. For example, the cardiac envelope may be set by default or in response to a user input to an endocardial surface, an epicardial surface, both epicardial and endocardial surfaces or another envelope having a user- or pre-defined 3D geometry.

In order to prepare the 3D geometry data for processing according to the n-dimensional MFS, the geometry processing system 300 also includes an n-dimensional translation function 320. The n-dimensional translation function 320 is programmed as instructions to convert the 3D geometry data 308 to the n-dimensional geometry data 302 in the n-dimensional domain (e.g., a 4D Cartesian coordinate system). For example, the translation function 320 converts the 3D cardiac envelope geometry and associated cardiac nodes 312 and the 3D body surface geometry 314 and associated body surface nodes 316 to corresponding geometry in a three-dimensional subspace of the n-dimensional domain. Within the three-dimensional subspace, the 3D spatial relationships between cardiac and body surface geometry are maintained; the subspace is placed by the translation function along a point in the n-dimensional space. While the example described above, describes determining cardiac and body surface nodes in 3D space and then translating them into n-dimensional space, in other examples, such nodes may be placed originally into the n-dimensional space. The n-dimensional data 302 may be stored as part of the geometry data 308 in memory (e.g., memory 102).

Figure 4:
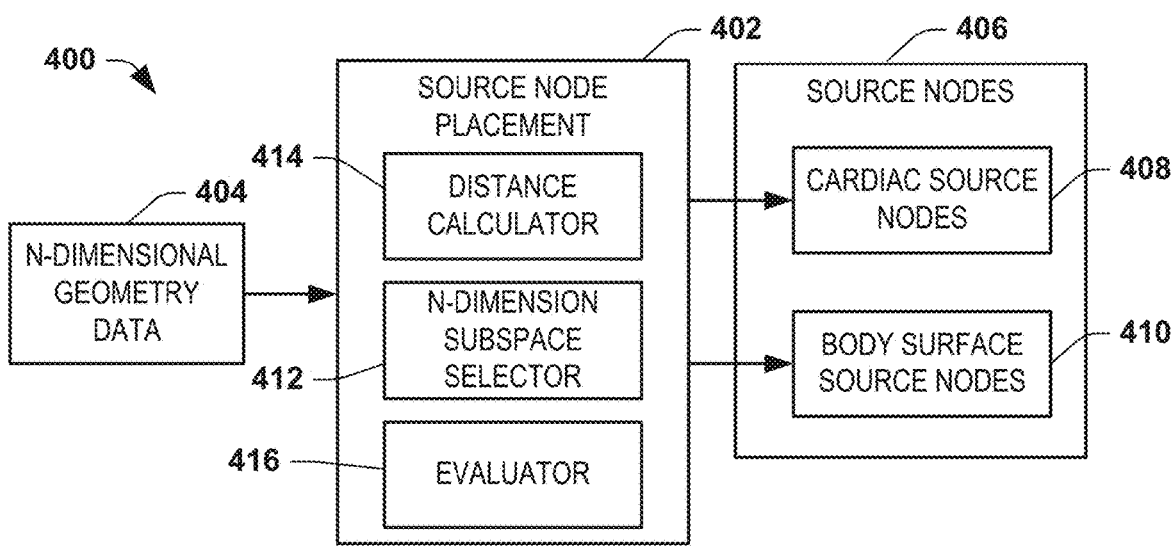
FIG. 4 depicts an example of placing source nodes in a spatial domain.

FIG. 4 depicts an example of a node placement system 400, such as may be implemented as machine-readable instructions and data stored in the memory and executable by the processor of FIG. 1. The system includes a node placement method 402 (e.g., corresponding to node placement 210) programmed to determine locations of source nodes 406 in n-dimensional space (e.g., 4D space) based on n-dimensional geometry data 404. The n-dimensional geometry data 404 can include cardiac envelope geometry (and cardiac nodes) and body surface geometry (body surface nodes) in a 3D subspace that has been placed along the nth dimension (e.g., data 302 generated by geometry processing system 300).

By way of example, the source node placement method 402 thus is programmed to determine the location of source nodes 406 in the nth dimension such that each source node, including each cardiac source node 408 and body surface nodes 410, is located a respective predetermined distance from each corresponding body surface node. For example, the source placement method 402 places the cardiac source nodes 408 in the nth dimension (e.g., 4th dimension) in a spatial distribution that corresponds to a spatial distribution of the cardiac nodes in the 3D subspace. Additionally, for example, the source placement method 402 places the torso source nodes in the nth dimension (e.g., 4th dimension) in a spatial distribution that corresponds to the spatial distribution of electrode locations on the body surface where the electrical activity is measured.

By way of further example, the source node placement method 402 first may generate the source node locations as coordinates in three-dimensional space, such as corresponding to the locations in the 3D spatial domain for the cardiac nodes and body surface nodes (e.g., in geometry data 308). A subspace selector 412 can place each of the cardiac source nodes in a different respective subspace of the nth dimension, which may be determined to satisfy distance and other constraints of the n-dimensional MFS in which source nodes must be placed outside of the volume conductor.

For example, the source node placement method 402 includes a distance calculator 414 to compute the distance between source nodes and the body surface nodes, such as for placing the cardiac source nodes and body surface source nodes with respect to the body surface nodes in connection with computing the transfer matrix A as disclosed herein. As another example, the source node placement method 402 utilizes the distance calculator 414 to compute the distance between source nodes and the cardiac surface nodes, such as for placing the cardiac source nodes and body surface source nodes with respect to the cardiac nodes on the cardiac envelope in connection with computing the transfer matrix B as disclosed herein.

An evaluator 416 may be programmed to evaluate the distance values between source nodes and respective body surface or cardiac nodes to meet desired distance criteria. In some examples, the evaluator 416 implements an optimization function (e.g., regression analysis) to determine the distance in n-dimensional space between the cardiac source nodes and the body surface nodes to approximate the distance between the torso source nodes and the body surface nodes.

Figures 5A, 5B:
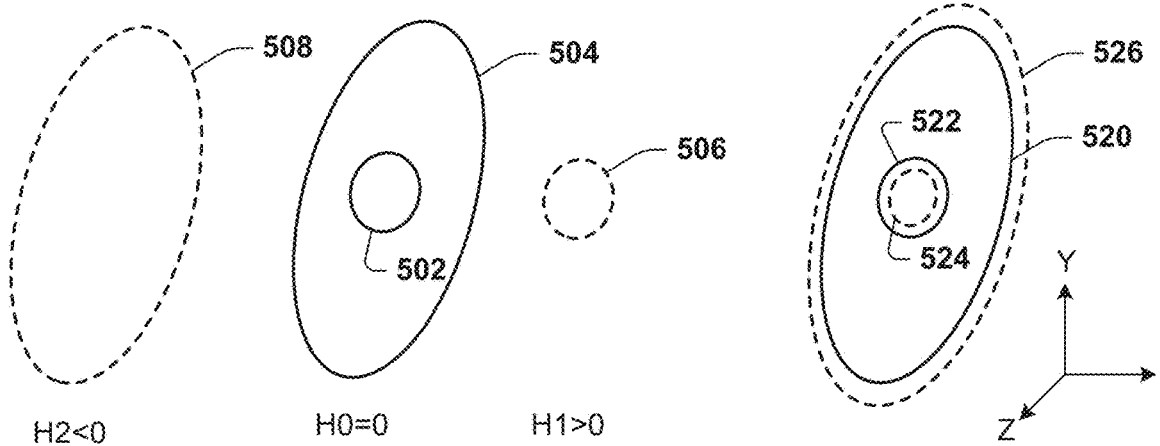
FIGS. 5A and 5B depict example spatial domains.

An example source node placement method 402 for use in implementing 4D MFS is demonstrated in FIG. 5A. Thus, for the example where n=4, 3D geometry for the cardiac envelope and associated cardiac nodes 502 and 3D geometry for the body surface and body surface nodes 504 collectively define a 3D subspace. This 3D subspace is placed (e.g., by subspace selector 412) at a given location along the $4^{th}$ dimension (e.g., at an origin location, H0=0). The 3D geometry for the cardiac source nodes 506, which defines another 3D subspace, is placed (e.g., by selector 412) at another location along the $4^{th}$ dimension (e.g., at location H1, where H1>0). The 3D geometry for the body surface source nodes 508, which defines yet another 3D subspace, is placed (e.g., by selector 412) at another location along the $4^{th}$ dimension (e.g., at location H2, where H2<0). In FIG. 5A, the H1 and H2 values correspond to source nodes associated with the heart and torso respectively. For example, the node placement method 402 can determine the values of H1 and H2 to make the 4D L2 distance from the source nodes associated with heart to the physical torso equal to the 4D L2 distance from the factious points associated with torso to the physical torso boundary. In other examples, different or same signs may be used for H1 and H2, such as including both H1>0 & H2>0, H1<0 & H2<0, H1<0 & H2>0. Additionally, or alternatively the H1 and H2 values can be different.

FIG. 5B demonstrates an example of the spatial relationship between body surface nodes 520, cardiac nodes 522 and fictitious cardiac source nodes 524 and body surface source nodes 526 as implemented according to 3D MFS. In such 3D MFS for reconstructing cardiac electrical activity, the cardiac source nodes are set inside of the cardiac surface of interest (e.g., epicardium) and the body surface source nodes are placed outside the body surface to comply with MFS rules of placing fictitious source points outside of the volume conductor. As a result, there tends to be difficulty in placing the fictitious source nodes within atrium and ventricular myocardium wall due to the small and irregular space available in 3D space. By contrast, the n-dimensional (e.g., 4D) MFS disclosed herein affords greater flexibility to place the fictitious source nodes in the nth dimension without violating the MFS rules of placing fictitious source points outside of the volume conductor. As disclosed herein, the fundamental solution to Laplace equation also has a nice analytical form $1/r^2$ in 4D, compared with $1/r$ in 3D space.

Figure 6:
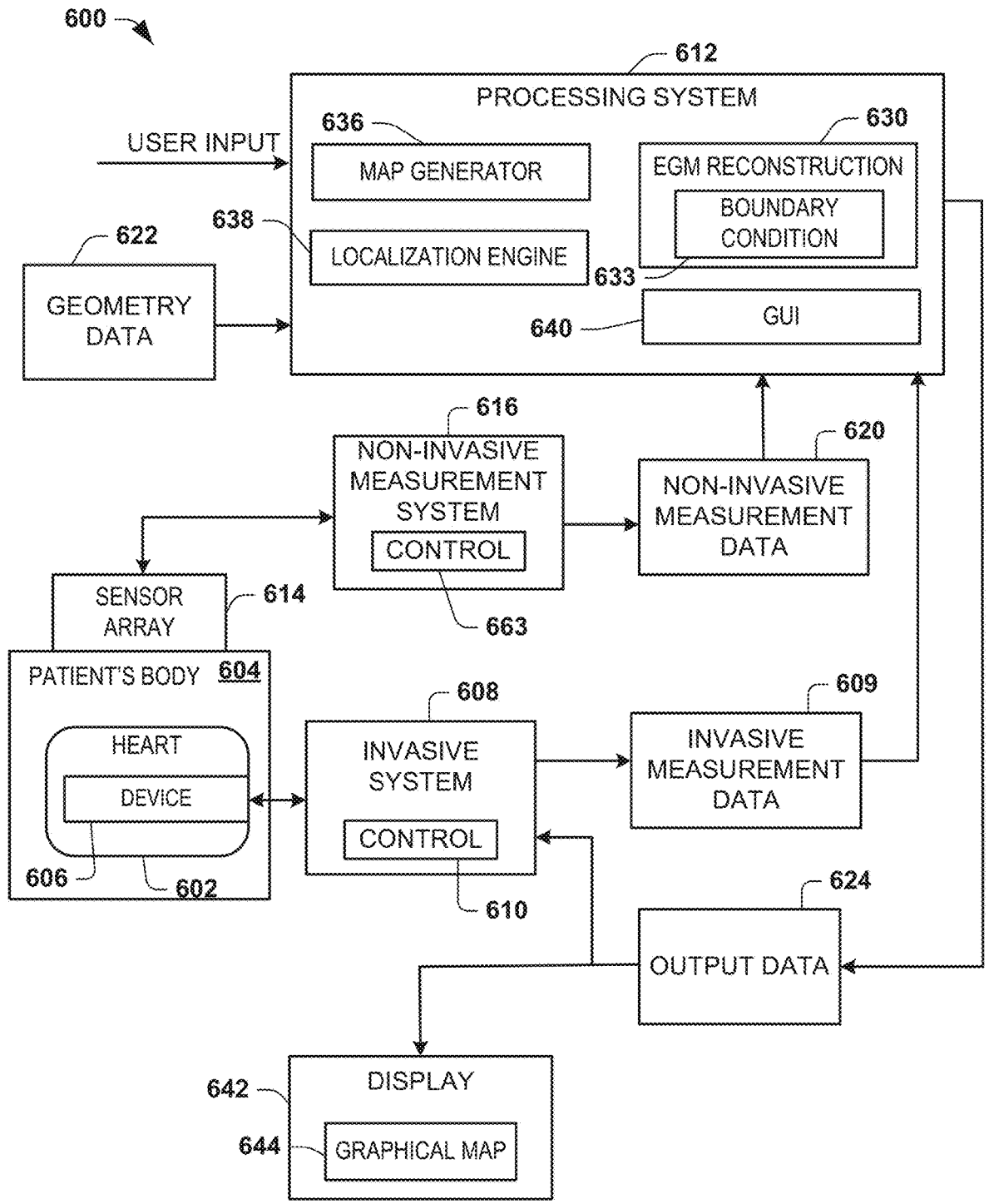
FIG. 6 depicts an example of a system for treatment and/or diagnosis.

FIG. 6 depicts an example of a system 600 that can be utilized for performing diagnostics and/or treatment of a patient. In some examples, the system 600 can be implemented to generate corresponding graphical outputs for signals and/or graphical maps for a patient's heart 602 in real time as part of a diagnostic procedure (e.g., monitoring of signals during an electrophysiology study) to help assess the electrical activity for the patient's heart. Additionally or alternatively, the system 600 can be utilized as part of a treatment procedure, such as to help a physician determine parameters for delivering a therapy (e.g., delivery location, amount and type of therapy) and provide a visualization and/or other output to facilitate determining when to end the procedure.

For example, an invasive device 606, such as a pacing catheter, having one or more electrodes affixed thereto can be inserted into a patient's body 604. The electrode can contact or not contact the patient's heart 602, endocardially or epicardially. The placement of the device 606 can be guided via a localization engine 638, which can operate to localize the device 606 employing an equivalent dipole model and measurements, as disclosed herein. The guidance can be automated, semi-automated or be manually implemented based on information provided. Those skilled in the art will understand and appreciate various type and configurations of devices 606, which can vary depending on the type of treatment and the procedure. The localization engine 638 thus can localize the device 606 and provide coordinates for the device and its electrodes, as disclosed herein.

For example, the device 606 can include one or more electrodes disposed thereon at predetermined locations with respect to the device. Each such electrode can be positioned with respect to the heart 602 via the device 606 and apply an electrical signal (e.g., a waveform) that can be measured by a plurality of sensors (e.g., in non-invasive sensor array 614 or another invasive device 606) located at known locations in a three-dimensional coordinate system. The sensors thus can sense electrical activity corresponding to each applied signal. The sensors can also sense other electrical signals, such as corresponding to real-time electrograms for the patient's heart 602. An invasive system 608 can include a control 610 configured to process (electrically) and control the capture of the measured signals as to provide corresponding invasive measurement data 609.

By way of example, the device 606 can be configured to deliver an electrical signal, which can be localized. The device 606 can apply the signal as to deliver a localization specific therapy, such as ablation, a pacing signal or to deliver another therapy (e.g., providing electrical therapy, or controlling delivery of chemical therapy, sound wave therapy, or any combination thereof). For instance, the device 606 can include one or more electrodes located at a tip of a pacing catheter, such as for pacing the heart, in response to electrical signals (e.g., pacing pulses) supplied by the system 608. Other types of therapy can also be delivered via the system 608 and the device 606 that is positioned within the body. The therapy delivery means can be on the same catheter or a different catheter probe than is used for sensing electrical activity.

As a further example, the system 608 can be located external to the patient's body 604 and be configured to control therapy that is being delivered by the device 606. For instance, the system 608 can also control electrical signals provided via a conductive link electrically connected between the delivery device (e.g., one or more electrodes) 606 and the system 608. The control system 610 can control parameters of the signals supplied to the device 606 (e.g., current, voltage, repetition rate, trigger delay, sensing trigger amplitude) for delivering therapy (e.g., ablation or stimulation) via the electrode(s) on the invasive device 606 to one or more location on or inside the heart 602. The control circuitry 610 can set the therapy parameters and apply stimulation or other therapy based on automatic, manual (e.g., user input) or a combination of automatic and manual (e.g., semiautomatic) controls. One or more sensors (not shown but could be part of the device) can also communicate sensor information back to the control 610.

Before, during and/or after delivering a therapy (e.g., via the system 608), one or more of the measurement systems 608 or 616 can be utilized to acquire electrophysiology information for the patient. In the example of FIG. 6, a sensor array 614 includes one or more sensors that can be utilized non-invasively for measuring patient electrical activity. As one example, the sensor array 614 can correspond to a high-density arrangement of body surface sensors that are distributed over a portion of the patient's outer body surface (e.g., thorax) for measuring electrical activity associated with the patient's heart (e.g., as part of an electrocardiographic mapping procedure).

An example of a non-invasive sensor array 614 that can be used is shown and described in International Application No. PCT/US2009/063803, filed 10 Nov. 2009, which is incorporated herein by reference. Other arrangements and numbers of sensors can be used as the sensor array 614. As an example, the array can be a reduced set of sensors, which does not cover the patient's entire torso and is designed for measuring electrical activity for a particular purpose (e.g., an arrangement of electrodes specially designed for analyzing AF and/or VF) and/or for monitoring a predetermined spatial region of the heart.

The electrical signals (e.g., potentials) measured non-invasively via the array 614 are provided to the measurement system 616. The measurement system 616 can include appropriate controls and signal processing circuitry 618 for providing corresponding measurement data 620 that describes electrical activity measured by the electrodes in the sensor array 614. The measurement data 620 can include analog and/or digital information (e.g., corresponding to electrical data 106).

The non-invasive measurement control 618 can also be configured to control the data acquisition process (e.g., sample rate, line filtering) for measuring electrical activity and providing the non-invasive measurement data 620. In some examples, the control 618 can control acquisition of measurement data 620 separately from the therapy system operation, such as in response to a user input. In other examples, the measurement data 620 can be acquired concurrently with and in synchronization with delivering therapy, such as to detect electrical activity of the heart 602 that occurs in response to applying a given therapy (e.g., according to therapy parameters) or specific signals applied for purposes of localization.

A processing system 612 includes an electrogram reconstruction method 630 (e.g., corresponding to reconstruction methods 110, 202), which is programmed to reconstruct electrical activity on a cardiac envelope by using an n-dimensional MFS 633, such as disclosed herein. For example, the n-dimensional MFS is programmed to perform an inverse computation and a forward computation based on n-dimensional geometry, which includes nodes on physical boundaries as well as source nodes at fictitious (e.g., virtual) points to determine corresponding reconstructed electrograms, which can be determined as disclosed herein. The reconstructed electrograms thus can correspond to electrocardiographic activity across a cardiac envelope, and can include static (electroanatomical map at a given instant in time) and/or be dynamic (e.g., an electroanatomical map that varies over time). The reconstruction method 630 thus can reconstruct the body surface electrical activity measured via the sensor array 614 onto a multitude of nodes on a cardiac envelope (e.g., 100 locations, greater than 1000 locations, such as about 2000 locations or more), which can be set a resolution of the reconstruction to a default value or set in response to a user input (via GUI 640), such as disclosed herein.

Since, in some examples, the measurement system 616 can measure electrical activity of a predetermined region or the entire heart concurrently (e.g., where the sensor array 614 covers the entire thorax of the patient's body 604), the accuracy in the resulting output location data 624 can be increased when compared to other localization techniques, such as to supply the user with a more accurate and global information to facilitate monitoring and application of therapy. Additionally or alternatively, the localization can be continuous process and/or be synchronized with respect to the application of therapy provided by the system 608.

As disclosed herein, the cardiac envelope can correspond to a three dimensional surface geometry corresponding to a patient's heart, which surface can be epicardial and/or endocardial. Alternatively or additionally, the cardiac envelope can correspond to a geometric surface that resides between the epicardial surface of a patient's heart and the surface of the patient's body where the sensor array 614 has been positioned. Additionally, the geometry data 622 that is utilized by the electrogram reconstruction 630 can correspond to actual patient anatomical geometry, a preprogrammed generic model or a combination thereof (e.g., a model that is modified based on patient anatomy).

As an example, the geometry data 622 may be in the form of graphical representation of the patient's torso, such as derived from processing image data acquired for the patient. Such image processing can include extraction and segmentation of anatomical features, including one or more organs and other structures, from a digital image set. Additionally, a location for each of the electrodes in the sensor array 614 can be included in the geometry data 622, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array in the coordinate system, such as a digitizer or manual measurements. As mentioned above, the geometry data 622 can correspond to a mathematical model, such as can be a generic model or a model that has been constructed based on image data for the patient.

A map generator 636 can generate corresponding output data 624 that can in turn be rendered as a corresponding graphical map 644 in a display 642, such as including electrical activity reconstructed on the cardiac envelope or electrical characteristics derived from such reconstructed electrical activity, as mentioned above. The electrical activity or derivations thereof can be displayed on graphical model of patient anatomy or superimposed on the electrocardiographic map 644.

Additionally, in some examples, the output data 624 can be utilized by the system 608 in connection with controlling delivery of therapy or monitoring electrical characteristics. The control 610 that is implemented can be fully automated control, semi-automated control (partially automated and responsive to a user input) or manual control based on the output data 624. In some examples, the control 610 of the therapy system can utilize the output data to control one or more therapy parameters. In other examples, an individual can view the map 644 generated on the display 642 to manually control the therapy system at a location determined based on this disclosure. Other types of therapy and devices can also be controlled based on the output data 624 and corresponding graphical map 644.

Figure 7:
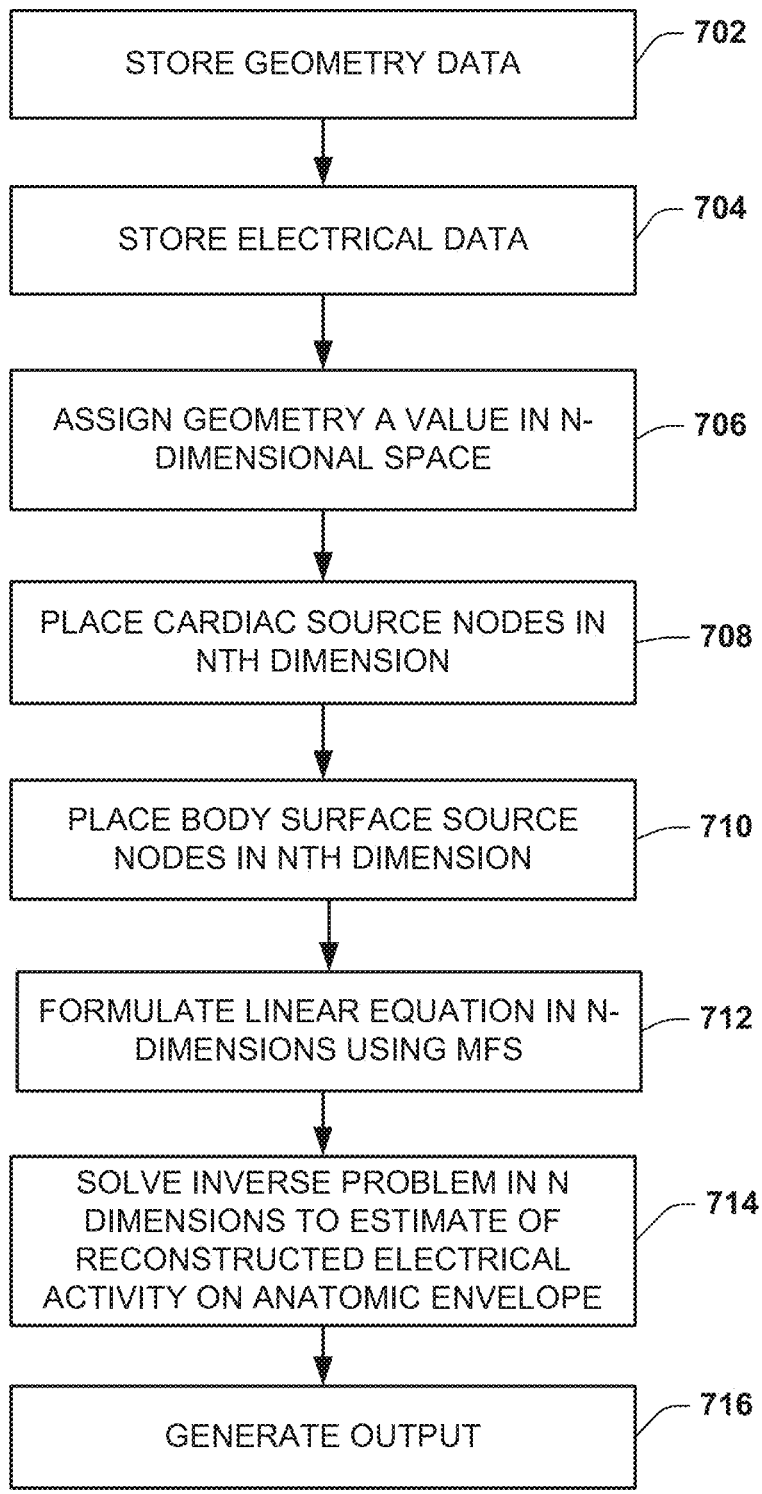
FIG. 7 is a flow diagram of an example method for reconstructing electrical activity.

In view of the foregoing structural and functional features described above, a method that can be implemented will be better appreciated with reference to flow diagram of FIG. 7. While, for purposes of simplicity of explanation, the method of FIG. 7 is shown and described as executing serially, it is to be understood and appreciated that such methods are not limited by the illustrated order, as some aspects could, in other examples, occur in different orders and/or concurrently with other aspects from that disclosed herein. Moreover, not all illustrated features may be required to implement a method. The methods or portions thereof can be implemented as instructions stored in a non-transitory machine readable medium as well as be executed by one or more processor of a computer device, for example.

FIG. 7 depicts an example of a method 700 to reconstruct electrical activity on an envelope. As disclosed herein the method uses an n-dimensional MFS to compute reconstructed electrical activity on a cardiac envelope. At 702, the method includes storing geometry data (e.g., data 108, 206, 308, 302, 404, 622) representing three-dimensional body surface geometry for the locations distributed on the body surface where the electrical activity is measured and three-dimensional heart geometry for the cardiac envelope. As disclosed, herein the cardiac envelope may include an endocardial surface, an epicardial surface, a combination of endocardial and epicardial surfaces or another 3D envelope of interest. At 704, electrical data (e.g., data 106, 208, 620) is stored. The electrical data includes a representation of electrical activity measured non-invasively from a plurality of locations distributed on a body surface of a patient over one or more time intervals. The electrical data may be real time data acquired during a study or previously acquired from a previous study, for example. In some examples, the non-invasive data may be supplemented with invasively measured electrical signals (e.g., data 609). The electrical and geometry data can be stored in a non-volatile or volatile memory structure, which may be local memory or distributed (e.g., in a network system).

At 706, the geometry is assigned a value in n-dimensional space. For example, the geometry data may be generated in 3D space and translated (e.g., by translator 320) into n-dimensional space (e.g., as a 3D subspace placed along 4D space). At 708 cardiac source nodes are placed (e.g., by placement method 210 or 402) in the nth dimension. At 710, body surface source nodes are placed (e.g., by placement method 210 or 402) in the nth dimension. The placement of source nodes may be controlled as a function of distance between source nodes and respective physical boundary nodes, such as disclosed herein.

At 712, linear equation is formulated in n-dimensions using MFS. For example the formulation may include deriving an analytical expression for the method of fundamental solution that includes a matrix A, which relates a location of each body surface source node to the locations distributed on the body surface where the electrical activity is measured and relates a location of each cardiac source node to the locations on the cardiac envelope for which the reconstructed cardiac electrical activity is to apply.

At 714, the inverse problem is solved in n dimensions to estimate reconstructed electrical activity on the cardiac envelope. For example, an inverse computation is performed on the A matrix and the noninvasively measured electrical activity to compute a plurality of source node coefficients. The formulation further may include determining a matrix of coefficients B that relates a location of each cardiac node on the cardiac envelope to each source node location. A forward computation is then performed using B and the plurality of source node coefficients to compute the reconstructed electrical activity on the cardiac envelope. The electrical activity may be computed for a plurality of time samples over one or more time intervals, such as by repeating 706-714.

At 716, an output is generated based on the reconstructed electrical activity that is computed. For example the output generated at 716 may include displaying a graphical visualization of cardiac electrical activity on the cardiac envelope based on the reconstructed electrical activity.

Figure 8:
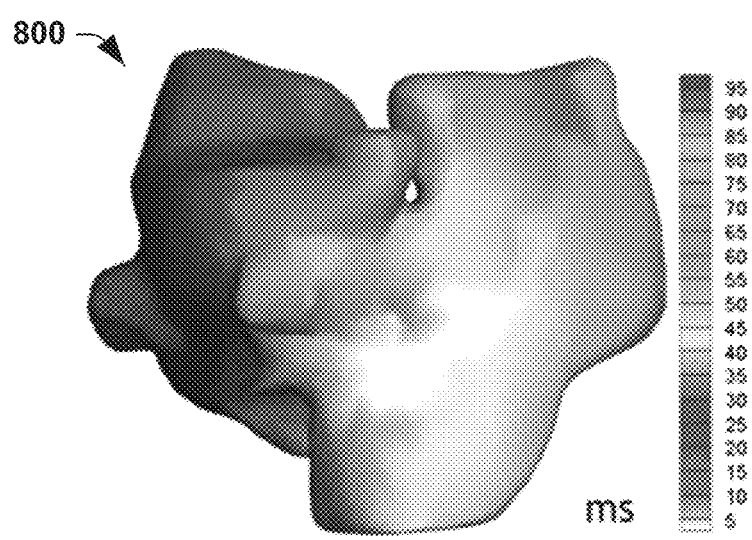
FIG. 8 depicts an example of an isochrone map for a cardiac surface.

FIG. 8 depicts an example of an isochrone map 800 of cardiac activation patterns that is generated using 4D MFS to reconstruct cardiac electrical activity for a cardiac surface over a time interval. The map 800 is able to accurately capture the earliest activation in an atrial tachycardia case, which in this example is at the right inferior pulmonary vein. Thus, the application of the systems and methods disclosed herein enables 4D-MFS reconstructed activation patterns that are much closer to activation maps measured invasively during the ablation procedure.

Figure 9A:
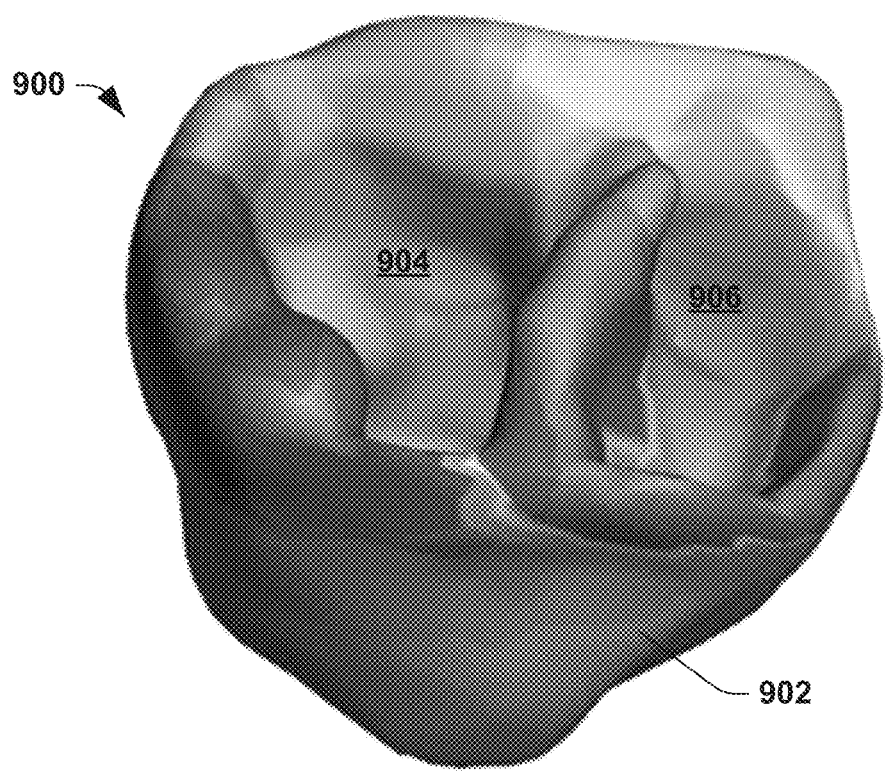
FIGS. 9A and 9B depict examples of isochrone maps generated from reconstructed electrical activity for both epicardial and endocardial surfaces.
Figure 9B:
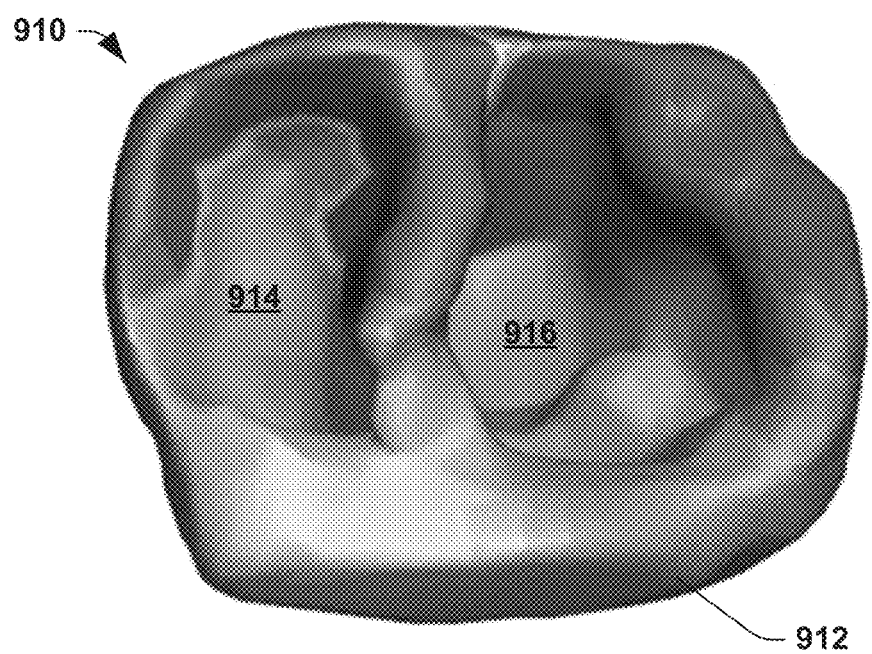

FIGS. 9A and 9B depict examples of isochrone maps 900 and 910 generated from reconstructed electrical activity for a normal sinus rhythm using 4D MFS. In the example of FIG. 9A, the isochrones map includes activation pattern for both epicardial 902 and endocardial surfaces 904 and 906. Similarly, FIG. 9B the isochrones map 910 includes activation patterns for both epicardial 912 and endocardial surfaces 914 and 916. This is in contrast to other reconstruction methods (e.g., BEM and original MFS), which are unable to reliably reconstruct the endocardial electrical activities. For example, concave mesh structure may be the causal factor in the failure of BEM based method, while thin myocardium wall geometry, leading to very limited space for original 3D MFS source nodes placement and optimization, may be the primary factor in the shortcomings of original 3D MFS methods. Thus, the n-dimensional (e.g., 4D) MFS disclosed herein affords better placement of fictitious source nodes in the 4D space, which can overcome limitations of original MFS method and thereby enable reconstructing electrical activity on the endocardial surface and other cardiac structures within the heart.

Figure 10:
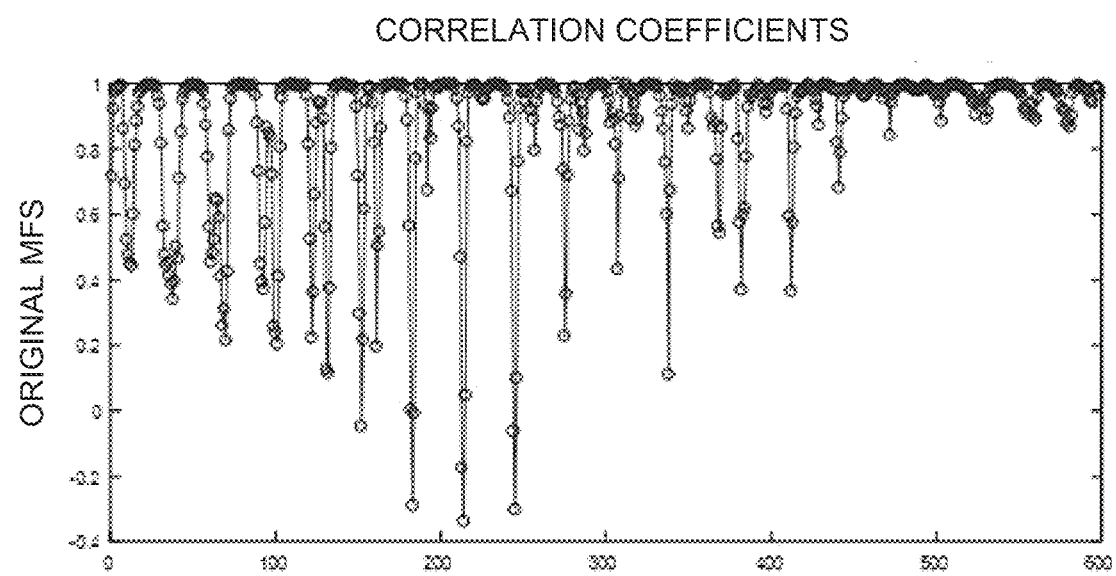
FIGS. 10 and 11 depict correlation coefficients and relative error associated with for reconstructed electrical activity generated according to an existing approach.
Figure 11:
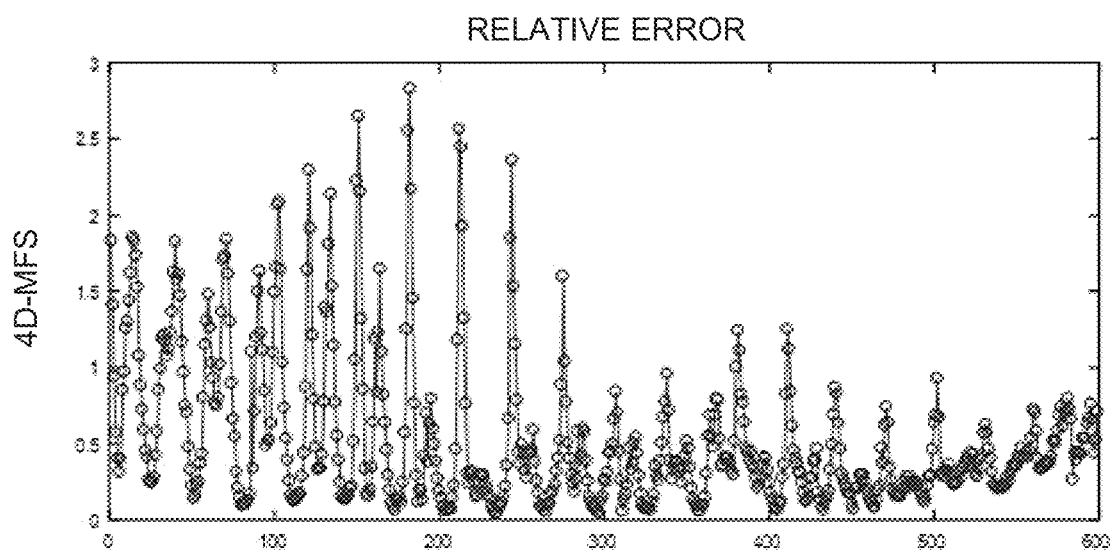
Figure 12:
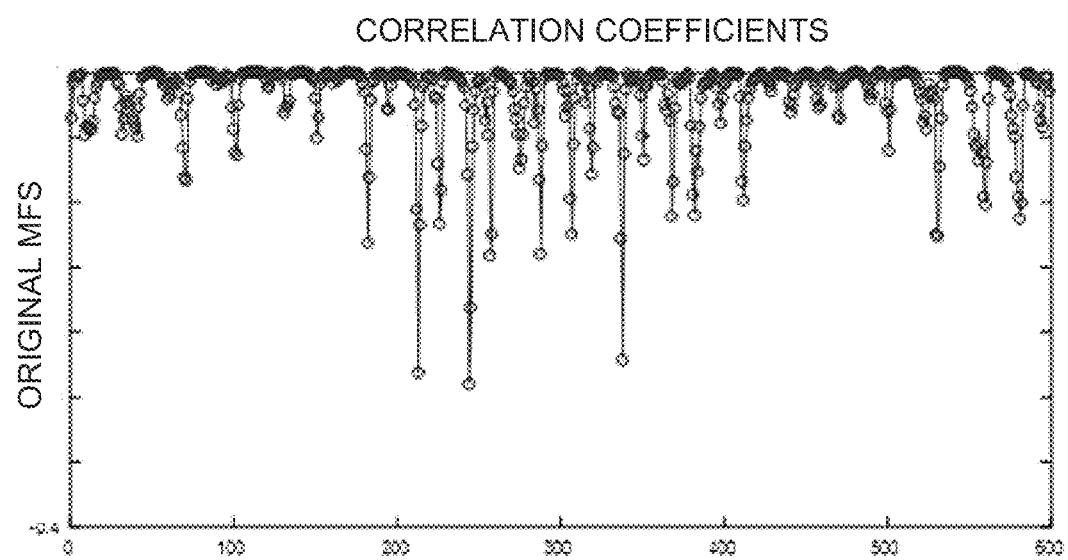
FIGS. 12 and 13 depict correlation coefficients and relative error associated with for reconstructed electrical activity generated according to a 4D meshless approach.
Figure 13:
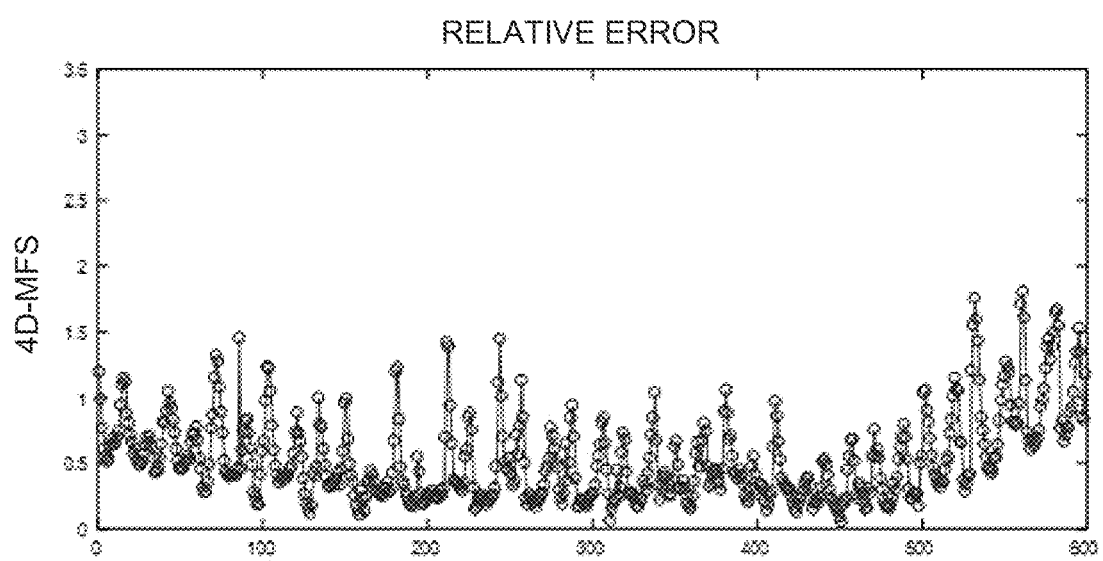

As a further example, FIGS. 10 and 11 depict correlation coefficients and relative error associated with for reconstructed electrical activity generated according to an existing approach. By comparison, FIGS. 12 and 13 depict correlation coefficients and relative error associated with for reconstructed electrical activity generated according to a 4D MFS, such as disclosed herein. As shown in FIG. 10-13, the 4D MFS reconstructed epicardial electrograms have higher correlation coefficient (measuring the morphology accruacy) and smaller relative error (measuring magnitude accuracy) compared to the orignial MFS reconstructed electrograms, confirming the feasibility and accuracy of 4D MFS.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, solid state storage, optical storage devices, and magnetic storage devices Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on."

What is claimed is:

1. A system comprising:
   memory to store data and executable instructions, the data including electrical data representing electrical activity measured from a plurality of locations distributed on a body surface, the data further including geometry data representing body surface geometry of the locations distributed on the body surface where the electrical activity is measured and geometry of a cardiac envelope; and
   at least one processor to access the memory and execute the instructions to at least:
   reconstruct electrical activity on to the cardiac envelope based on the geometry data and the electrical data, the reconstructed electrical activity being computed using an n-dimensional method of fundamental solution, where n is a positive integer greater than three.

2. The system of claim 1, further comprising:
   an arrangement of electrodes configured to measure the electrical activity from the plurality of locations distributed on the body surface; and
   a display configured to display a graphical visualization generated based on the reconstructed electrical activity.

3. The system of claim 1, wherein the processor executes the instructions to convert the geometry data, representing the body surface geometry and the geometry of the cardiac envelope in a three-dimensional spatial domain, to corresponding geometry in a three-dimensional subspace of an n-dimensional domain.

4. The system of claim 3, wherein the processor is further configured to:
   determine a plurality of cardiac nodes that define the locations on the cardiac envelope for which the reconstructed electrical activity applies;
   determine a plurality of source nodes in the n-dimensional domain outside of the corresponding the three-dimensional spatial domain, one plurality of the source nodes defines body surface source nodes in a first three-dimensional subspace of the n-dimensional domain and another plurality of the source nodes defines cardiac source nodes in a second three-dimensional subspace of the n-dimensional domain;

derive an analytical expression for the method of fundamental solution that includes a matrix A that relates a location of each body surface source node and cardiac source node to the locations distributed on the body surface where the electrical activity is measured and perform an inverse computation on the A matrix and the noninvasively measured electrical activity to compute a plurality of source node coefficients.

5. The system of claim 4, wherein the instructions are further configured to:

determine a matrix of coefficients B that relates each cardiac node location to each source node location; and perform a forward computation using B and the plurality of source node coefficients to compute the electrical activity on the cardiac envelope.

6. The system of claim 4, wherein the processor is further configured to:

determine the location of each body surface source node in the nth dimension such that it is located a predetermined distance from a corresponding location on the body surface where the electrical activity is measured, and determine the location of each cardiac source node in the nth dimension such that it is located a predetermined distance from a corresponding cardiac node location.

7. The system of claim 4, wherein the nth dimension is a fourth dimension, and wherein the cardiac source nodes are placed in the fourth dimension in a spatial distribution that corresponds to a spatial distribution of the cardiac nodes and the body surface source nodes are placed in the fourth dimension in a spatial distribution that corresponds to a spatial distribution of electrode locations on the body surface where the electrical activity is measured.

8. The system of claim 7, wherein a distance between the cardiac source nodes and the body surface approximates a distance between the body surface source nodes and the body surface.

9. The system of claim 7, wherein the value of each entry in the matrix A is calculated as a function of a square of a distance between each body surface node and each source node.

10. The system of claim 4, wherein the locations of the plurality of cardiac nodes are set, in response to a user input, to reside on a selected at least one of an epicardial surface and an endocardial surface.

11. The system of claim 1, wherein the processor is further configured to generate a graphical map of cardiac electrical activity from the reconstructed electrical activity.

12. The system of claim 11, wherein the cardiac envelope includes one of an epicardial surface and an endocardial surface.

13. The system of claim 11, wherein the cardiac envelope includes both of an epicardial surface and an endocardial surface.

14. The system of claim 11, wherein the cardiac envelope includes an epicardial surface, an endocardial surface and other structures inside the heart.

15. A method comprising:

using an n-dimensional method of fundamental solution, where n is a positive integer greater than three, to compute reconstructed electrical activity on a cardiac envelope based on geometry data and electrical data, wherein the electrical data represents electrical activity measured non-invasively from a plurality of locations distributed on a body surface of a patient, and the geometry data represents three-dimensional body surface geometry for the locations distributed on the body surface where the electrical activity is measured and three-dimensional heart geometry for the cardiac envelope.

16. The method of claim 15, further comprising:

measuring the electrical activity at the plurality of locations distributed on the body surface in a three-dimensional spatial domain over one or more time intervals; and displaying a graphical visualization of cardiac electrical activity on the cardiac envelope based on the reconstructed electrical activity.

17. The method of claim 15, further comprising:

converting the geometry data to represent the body surface geometry and the geometry of the cardiac envelope in a three-dimensional subspace along the nth dimension.

18. The method of claim 17, further comprising:

determining a plurality of cardiac nodes that define the locations in the geometry of the cardiac envelope for which the reconstructed electrical activity applies;

determining a plurality of body surface source nodes in the nth dimension at locations outside of the three-dimensional subspace;

determine a plurality of cardiac source nodes in the nth dimension outside of the three-dimensional subspace;

derive an derive analytical expression for the method of fundamental solution that includes a matrix A that relates a location of each body surface source node to the locations distributed on the body surface where the electrical activity is measured and relates a location of each cardiac source node to the locations on the cardiac envelope for which the reconstructed electrical activity applies; and perform an inverse computation on the A matrix and the noninvasively measured electrical activity to compute a plurality of source node coefficients.

19. The method of claim 18, further comprising:

determining a matrix of coefficients B that relates a location of each cardiac node to each source node location; and performing a forward computation using B and the plurality of source node coefficients to compute the reconstructed electrical activity on the cardiac envelope.

20. The method of claim 18, further comprising:

determining the location of each body surface source node such that it is located in the nth dimension a predetermined distance from a corresponding location on the body surface where the electrical activity is measured, and determining the location of each cardiac source node such that it is located in the nth dimension a predetermined distance from a corresponding cardiac node location.

21. The method of claim 18, wherein the nth dimension is a fourth dimension not corresponding to time, and wherein the cardiac source nodes are placed in the fourth dimension and the body surface source nodes are placed in the fourth dimension.

22. The method of claim 21, wherein a distance between the cardiac source nodes and the body surface approximates a distance between the body surface source nodes and the body surface.

23. The method of claim 21, wherein the value of each entry in the matrix A is calculated as a function of a square of a distance between each torso node and each source node.

24. The method of claim 18, further comprising:

receiving a user input selection; and setting the locations of the plurality of cardiac nodes, in response to the user input selection, to reside on at least one of an epicardial surface and an endocardial surface.

25. The method of claim 15, wherein the cardiac envelope includes at least one of an epicardial surface, an endocardial surface and other surface structures inside the heart.

26. One or more non-transitory computer-readable media having instructions which, when executed by a processor, perform the method of claim 15.

\* \* \* \* \*